United States Patent
Van Der Gucht et al.

(10) Patent No.: US 11,958,030 B2
(45) Date of Patent: Apr. 16, 2024

(54) COACERVATE CORE-SHELL MICROCAPSULES

(71) Applicant: Firmenich SA, Satigny (CH)

(72) Inventors: Jasper Van Der Gucht, Wageningen (NL); Renko De Vries, Wageningen (NL); Xiufeng Li, Wageningen (NL); Gregory Dardelle, Satigny (CH); Philipp Erni, Satigny (CH); Lahoussine Ouali, Satigny (CH); Nathalie Thiebaut, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 17/995,566

(22) PCT Filed: Mar. 24, 2021

(86) PCT No.: PCT/EP2021/057592
§ 371 (c)(1),
(2) Date: Oct. 5, 2022

(87) PCT Pub. No.: WO2021/191290
PCT Pub. Date: Sep. 30, 2021

(65) Prior Publication Data
US 2023/0149878 A1    May 18, 2023

(30) Foreign Application Priority Data
Mar. 27, 2020   (EP) .................................. 20166346

(51) Int. Cl.
*B01J 13/10*    (2006.01)

(52) U.S. Cl.
CPC .................................... *B01J 13/10* (2013.01)

(58) Field of Classification Search
None
See application file for complete search history.

(56) References Cited

U.S. PATENT DOCUMENTS

| 2004/0032036 A1* | 2/2004 | Subramaniam ........ A61Q 19/00 264/4.1 |
| 2004/0151778 A1* | 8/2004 | Richard ............... A61K 9/5089 424/490 |
| 2018/0078468 A1 | 3/2018 | Jerri et al. |

OTHER PUBLICATIONS

Jun-Xia X et al.: "Microencapsulation of sweet orange oil by complex coacervation with soybean protein isolate/gum Arabic", Food Chemistry, vol. 125, No. 4, pp. 1267-1272 (2011).
Klassen D R et al.: "Effect of pH on the formation of electrostatic complexes within admixtures of partially purified pea proteins (legumin and vicilin) and gum arabic polysaccharides", Food Research International, vol. 46, No. 1, pp. 167-176 (2012).
Yakindra Prasad Timilsena et al.: "Preparation and characterization of chia seed protein isolate-chia seed gum complex coacervates", Food Hydrocolloids, vol. 52, pp. 554-563 (2015).

\* cited by examiner

*Primary Examiner* — Jeffrey D Washville
(74) *Attorney, Agent, or Firm* — Armstrong Teasdale LLP (57) ABSTRACT

The present invention relates to plant-based coacervate core-shell microcapsules, wherein the shell comprises a plant protein extract, as well as methods and uses of the same.

18 Claims, 3 Drawing Sheets

COACERVATE CORE-SHELL MICROCAPSULES

This present application is a U.S. national phase entry under 35 U.S.C. § 371 of PCT Application No. PCT/EP2021/057592, filed Mar. 24, 2021, which claims priority to European Patent Application No. 20166346.5, filed Mar. 27, 2020. The entire contents of these applications are explicitly incorporated herein by this reference.

TECHNICAL FIELD

The present invention relates to plant-based coacervate core-shell microcapsules, wherein the shell comprises a plant protein extract, as well as methods and uses of the same.

BACKGROUND

Typical steps of coacervation processes generally involve (a) emulsification of a generally hydrophobic material in a solution comprising hydrocolloids, (b) coacervation (phase separation) implying the formation of a coacervate phase (c) wall formation by aggregation of the hydrocolloid around droplets of the emulsified hydrophobic material, and, (d) wall-hardening, which is generally achieved by cross-linking the hydrocolloid forming the wall thus rendering the process irreversible and making the resulting microcapsules insoluble in water, resistant to mechanical stress and to heat exposure.

The step of wall formation is generally driven by the surface tension difference between the coacervate phase, the water and the hydrophobic material. In most coacervation processes, one of the hydrocolloids used in coacervation processes is gelatin. The reasons for this traditional preference are (i) gelatin is generally easier to use since its rheological behaviour, structure and molecular configuration in solution and in gelled form can be easily controlled using the parameters of concentration and temperature, (see for example the publication by Norman et al. (Gelation Kinetics of Gelatin: A Master Curve and Network Modeling, Macromolecules 2000, 33, 3, 1063-1071), (ii) the control over these parameters allows the operator to choose process and formulation conditions such that the resulting coacervate remains liquid-like and deposit onto the to-be-encapsulated payload material, (iii) the resulting coacervate shell comprising gelatin can be easily made to gel by lowering the process temperature, thereby rapidly providing an initial physically crosslinked shell that protects the freshly generated capsules against shear and mixing, (iv) the gelation process of gelatin induced by lowering the temperature is fully reversible, as the phase separation step during which the coacervate is formed, allowing the operator to simply re-start the encapsulation process by heating up the system, (v) gelatin possesses ideal electrostatic properties to interact with the non-gelatin polymer during coacervation, thereby avoiding the formation of unseemly and non-processable precipitates or other types of aggregates, (vi) gelatin possesses ideal amphiphilic properties due to the protein primary and secondary structure imparted by its amino acid composition and sequence (vii) gelatin is less prone to aggregation after the formation of the wall when the temperature is below the gelling temperature, as compared to non-gellable hydrocolloids. All these aspects are intrinsic advantages of gelatin directly related to its molecular structure, which is due to its origin from hydrolysed animal collagen.

However, the use of capsules comprising gelatin is not possible in food consumer and food products wherein animal-sourced ingredients are not allowed due to regulatory, potential health hazard (mad cow disease or Bovine Spongiform Encephalopathy), cultural or religious restrictions. Moreover, it is often desirable to use plant-based ingredients compared to animal-derived ingredients for a better sustainability profile of the final consumer products, primarily due to the much more limited need for water for production of comparable amounts of proteins derived directly from plants, as compared to proteins derived from animal breeding. Simply replacing gelatin with a plant-based biopolymer to obtain coacervates with comparable properties is highly challenging, since the combination of all the advantages (i)-(vii) listed above is generally thought to be impossible to obtain by a simple replacement of gelatin with any protein or non-protein biopolymer or other food grade ingredient. In particular, the majority of plant proteins suitable for use as ingredients in foods and consumer products do not provide the required electrostatic, amphiphilic and gelation properties. In particular, plant-based proteins, and even milk proteins, do not allow to prepare a heated solution to be turned into a gel upon cooling, but rather form a partially or fully irreversible particle gel (a similar illustrative example for an animal-sourced protein is the coagulation of albumin, which is widely known to occur irreversible upon heating egg white.)

It would be therefore desirable to provide new plant-based coacervate microcapsules and also establish different ways of manufacturing microcapsules by coacervation.

DETAILED DESCRIPTION

Unless stated otherwise, percentages (%) are meant to designate a percentage by weight of a composition.

A first object of the invention is a coacervate core-shell microcapsule comprising a hydrophobic material, preferably a flavor or a perfume, wherein:
  the hydrophobic material is encapsulated in the core of the coacervate core-shell microcapsule, and
  the shell of the coacervate core-shell microcapsule comprises at least one plant protein extract and optionally a non-protein polymer.

Another object of the invention is a coacervate core-shell microcapsule slurry comprising at least one coacervate core-shell microcapsule comprising a hydrophobic material, preferably a flavor or a perfume, wherein:
  the hydrophobic material is encapsulated in the core of the coacervate core-shell microcapsule, and the shell of the coacervate core-shell microcapsule comprises at least one plant protein extract and optionally a non-protein polymer.

By "coacervate core-shell microcapsule", it should be understood a microcapsule comprising an oily or solid-like core material (the "hydrophobic material") surrounded by a hydrogel shell comprising a coacervate material (also called "membrane" or "coating layer"). The core material can be partially or totally surrounded by the hydrogel shell.

Preferably, the coacervate core-shell microcapsules of the present invention comprises a core which is completely surrounded by a coacervate shell. According to this embodiment, it is understood that the core is completely encapsulated by a coacervate shell.

Preferably, the coacervate core-shell microcapsule has a degree of cross-linking between 10 and 70% following the method described in Soft Matter, 2011, 7, 3315-3322 (Determination of covalent cross-linker efficacy of gelatin strands using calorimetric analyses of the gel state).

According to a particular embodiment, the coacervate core-shell microcapsules has a rupture force between 0.01 and 10 N, preferably between 0.1 and 2 N. The rupture force can be measured by compression of the capsule between parallel plates in a mechanical testing instrument, for example a Texture Analyzer (Food Technology Corporation, USA), an Instron Mechanical Testing machine (Instron, USA) or also using a rheometer device equipped with a normal force transduced (e.g. DHR-2 Rheometer manufactured by TA Instruments, USA or MCR Rheometer manufacture by Anton Paar GmbH, Germany).

The coacervate core-shell microcapsules may have a median capsule size of from 5 to 1000 μm, preferably from 100 μm to 800 μm, more preferably from 200 μm to 600 μm, even more preferably from 250 μm to 450 μm. The median microcapsule size of the coacervate core-shell microcapsules can be determined by standard laser diffraction particle size analysis or by light microscopy combined with image analysis. Here, for present invention, the microcapsule size refers to values based on number-based size distributions as measured by light microscopy (e.g. with a Nikon TE2000 microscope) and image analysis (performed with Nikon NIS Elements Software). Methods to obtain median and average size distributions are described in the scientific literature, e.g. R. J. Hunter, "Introduction to Modern Colloid Science", Oxford University Press, 1994).

The coacervate core-shell microcapsules may be made by "simple" and by "complex" coacervation. By simple coacervation it is understood that the plant protein extract alone made to undergo phase separation and is then used to form a capsule wall. By complex coacervation are understood methods in which a non-protein polymer and plant protein extract together form the microcapsule shell.

According to a particular embodiment, the coacervate core-shell microcapsules are made by "complex" coacervation.

According to the invention, the shell of the core-shell microcapsules comprises at least one plant protein extract. The shell can comprise a plant protein extract or a mixture of plant protein extracts.

By "plant protein extract", it should be understood an extract preferably obtained from an extraction of pulse seeds, pulse seed flour or root vegetables, more preferably obtained from an acidic extraction of pulse seeds, pulse seed flour or root vegetables.

According to an embodiment, the plant protein extract is an extract obtained from an extraction of pulse seeds, preferably an acidic extraction of pulse seeds.

According to an embodiment, the plant protein extract is a legume extract and is obtained from an extraction of a legume flour.

According to an embodiment, the plant protein extract is an acidic plant protein extract.

According to an embodiment, the plant protein extract is a basic plant protein extract.

According to the invention a "plant protein extract" or a "plant protein concentrate" is used indifferently. Typically, the content of the protein contained in the extract (or the concentrate) is less than 55% by weight.

Contrary to an isolate, the extract is not obtained by using further purification steps (such as ion exchange or membrane filtration) beyond the extraction step itself. According to the invention, a plant protein extract is not a plant protein isolate. Indeed, contrary to an isolate comprising a high amount of protein (typically greater than 80%), the content of the protein contained in the extract (or the concentrate) is less than 55% by weight. Contrary to an isolate, in the extract may be retained additional constituents that would be lost by preparation of an isolate, such as soluble and insoluble carbohydrates and lipids including phospholipids. Such additional constituents may be favorable for providing density and/or nutritional value to the materials prepared.

According to an embodiment, the plant protein extract comprises carbohydrates and/or lipids.

Indeed, a key advantage of the present invention compared to using known protein isolates is that the mild extraction of pulse seed flour (or pulse seeds or root vegetables) does not impart the damaging denaturation onto the proteins, leaving the protein sufficiently intact to undergo complex coacervation.

According to an embodiment, the plant protein extract is chosen in the group consisting of protein extracts from soy, pea, wheat, rice, potato, quinoa, amaranth, lentil, hemp, oat, buckwheat, chick pea, lupin seeds, canola, flaxseed and mixtures thereof.

According to an embodiment, the content of globulin contained in the extract is comprised between 0 and 75% w/w, preferably between 5 and 35% w/w.

According to an embodiment, the shell of the core-shell microcapsules also comprises a non-protein polymer in addition to the plant protein extract.

The non-protein polymer may be chosen in the group consisting of gum arabic, carboxymethylcellulose, chitosan, xanthan, agar, alginate salts, pectinate salts or carrageenan, preferably wherein the non-protein polymer is gum arabic.

According to a particular embodiment, the non-protein polymer is chitosan.

Further suitable non-proteins can be derived from the literature, for example De Kruif et al., Current Opinion in Colloid and Interface Science, Vol. 9, pp 340-349, 2004.

According to a particular embodiment, the plant protein extract is a soy protein extract and the non-protein polymer is Gum Arabic.

According to an embodiment, the weight ratio between the plant protein extract and the non-protein polymer is comprised between 1 and 100, particularly between 1 and 10, more particularly between 1 and 5.

According to a Particular Embodiment the plant protein extract is soy protein extract and the non-protein polymer is gum arabic, and the ratio between plant protein extract and the non-protein polymer is from 1:0.7 to 1:0.3.

According to a Particular Embodiment the plant protein extract is pea protein extract and the non-protein polymer is gum arabic, and the ratio between plant protein extract and the non-protein polymer is from 1:0.3 to 1:0.1.

According to an embodiment, the coacervate shell is free from animal proteins.

According to an embodiment, the coacervate shell is free from gelatin.

According to the present invention, the coacervate core-shell microcapsule comprises a hydrophobic material.

According to an embodiment, the hydrophobic material is a hydrophobic active ingredient.

By "hydrophobic active ingredient", it is meant any hydrophobic active ingredient—single ingredient or a mixture of ingredients—which forms a two-phase dispersion when mixed with water. The hydrophobic active ingredient is preferably liquid at about 20° C.

By "active ingredient", it is meant a single compound or a combination of ingredients.

By "perfume or flavour oil", it is meant a single perfuming or flavouring compound or a mixture of several perfuming or flavouring compounds.

Hydrophobic active ingredients are preferably chosen from the group consisting of flavor, flavor ingredients, perfume, perfume ingredients, nutraceuticals, cosmetics, pest control agents, biocide actives and mixtures thereof.

According to a particular embodiment, the hydrophobic active ingredient comprises a mixture of a perfume with another ingredient selected from the group consisting of nutraceuticals, cosmetics, pest control agents and biocide actives.

According to a particular embodiment, the hydrophobic active ingredient comprises a mixture of biocide actives with another ingredient selected from the group consisting of perfume, nutraceuticals, cosmetics, pest control agents.

According to a particular embodiment, the hydrophobic active ingredient comprises a mixture of pest control agents with another ingredient selected from the group consisting of perfume, nutraceuticals, cosmetics, biocide actives.

According to a particular embodiment, the hydrophobic active ingredient comprises a perfume.

According to a particular embodiment, the hydrophobic active ingredient consists of a perfume.

According to a particular embodiment, the hydrophobic active ingredient comprises a flavour.

According to a particular embodiment, the hydrophobic active ingredient consists of a flavor.

By "perfume" (or also "perfume oil") what is meant here is an ingredient or composition that is preferably a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, pest control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said ingredients may also be compounds known to release in a controlled manner various types of perfuming compounds.

In particular one may cite perfuming ingredients which are commonly used in perfume formulations, such as:

Aldehydic ingredients: decanal, dodecanal, 2-methyl-undecanal, 10-undecenal, octanal, nonanal and/or nonenal;

Aromatic-herbal ingredients: eucalyptus oil, camphor, eucalyptol, 5-methyltricyclo[6.2.1.0~2,7~]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4 (2H)-pyranol, beta ionone, methyl 2-(methylamino) benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1 S)-1-[(1R)-3,3-dimethylcyclohexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclohexyl) ethoxycarbonyl]methyl propanoate, Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R, E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

It is also understood that said ingredients may also be compounds known to release in a controlled manner various types of perfuming compounds also known as properfume or profragrance. Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-(dodecylthio)octan-4-one, 2-phenylethyl oxo(phenyl)acetate, 3,7-dimethylocta-2,6-dien-1-yl oxo(phenyl)acetate, (Z)-hex-3-en-1-yl oxo(phenyl)acetate, 3,7-dimethyl-2,6-octadien-1-yl hexadecanoate, bis(3,7-dimethylocta-2,6-dien-1-yl) succinate, (2-((2-methylundec-1-en yl)oxy)ethyl)benzene, 1-methoxy-4-(3-methyl-4-phenethoxybut-3-en-1-yl) benzene, (3-methyl phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en yl)benzene, 2-(1-phenethoxyprop-1-en-2-yl)naphthalene, (2-phenethoxyvinyl)benzene, 2-(1-((3,7-dimethyloct-6-en-1-yl)oxy)prop-1-en-2-yl)naphthalene, (2-((2-pentylcyclopentylidene)methoxy)ethyl)benzene or a mixture thereof.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Preferred perfuming ingredients are those having a high steric hindrance and in particular those from one of the following groups:

Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one C7 to C20 ring structure;

Group 7: perfuming ingredients having a log P value above 3.5 and comprising at least one tert-butyl or at least one trichloromethyl substitutent;

Examples of ingredients from each of these groups are:

Group 1: 2,4-dimethyl-3-cyclohexene-1-carbaldehyde (origin: Firmenich S A, Geneva, Switzerland), isocyclocitral, menthone, isomenthone, methyl 2,2-dimethyl-6-methylene cyclohexanecarboxylate (origin: Firmenich S A, Geneva, Switzerland), nerone, terpineol, dihydroterpineol, terpenyl acetate, dihydroterpenyl acetate, dipentene, eucalyptol, hexylate, rose oxide, (S)-1,8-p-menthadiene-7-ol (origin: Firmenich S A, Geneva, Switzerland), 1-p-menthene-4-ol, (1 RS,3RS, 4SR)-3-p-mentanyl acetate, (1R,2S,4R)-4,6,6-trimethyl-bicyclo[3,1,1]heptan-2-ol, tetrahydro-4-methyl-2-phenyl-2H-pyran (origin: Firmenich S A, Geneva, Switzerland), cyclohexyl acetate, cyclanol acetate, 1,4- cyclohexane diethyldicarboxylate (origin: Firmenich S A, Geneva, Switzerland), (3ARS,6SR,7ASR)-perhydro-3,6-dimethyl-benzo[B]furan-2-one (origin: Firmenich S A, Geneva, Switzerland), ((6R)-perhydro-3,6-dimethyl-benzo[B]furan-2-one (origin: Firmenich S A, Geneva, Switzerland), 2,4,6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yl)-2-buten-1-ol (origin: Firmenich S A, Geneva, Switzerland), (1'R,E)-3,3-dimethyl-5-(2',2',3'-trimethyl-3'-cyclopenten-1'-yl)-4-penten-2-ol (origin: Firmenich S A, Geneva, Switzerland), 2-heptylcyclopentanone, methyl-cis-3-oxo-2-pentyl-1-cyclopentane acetate (origin: Firmenich SA, Geneva, Switzerland), 2,2,5-Trimethyl-5-pentyl-1-cyclopentanone (origin: Firmenich S A, Geneva, Switzerland), 3,3-dimethyl-5-(2,2,3-trimethyl-3-cyclopenten-1-yl)-4-penten-2-ol (origin: Firmenich S A, Geneva, Switzerland), 3-methyl-5-(2,2,3-trimethyl-3-cyclopenten-1-yl)-2-pentanol (origin, Givaudan S A, Vernier, Switzerland);

Group 3: damascones, 1-(5,5-dimethyl-1-cyclohexen-1-yl)-4-penten-1-one (origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, mixture of 1-(5,5-dimethyl-1-cyclohexen-1-yl)-4-penten-1-one and 1-(3,3-dimethyl-1-cyclohexen-1-yl)-4-penten-1-one (origin: Firmenich S A, Geneva, Switzerland), 1-(2,6,6-trimethyl-1-cyclohexen-1-yl)-2-buten-1-one (origin: Firmenich S A, Geneva, Switzerland), (1S,1'R)-[1-(3',3'-Dimethyl-1'-cyclohexyl)ethoxycarbonyl]methyl propanoate (origin: Firmenich S A, Geneva, Switzerland), 2-tert-butyl-1-cyclohexyl acetate (origin: International Flavors and Fragrances, USA), 1-(2,2,3,6-tetramethyl-cyclohexyl)-3-hexanol (origin: Firmenich S A, Geneva, Switzerland), trans-1-(2,2,6-trimethyl-1-cyclohexyl)-3-hexanol (origin: Firmenich S A, Geneva, Switzerland), (E)-3-methyl-4-(2,6,6-trimethyl-2-cyclohexen-1-yl)-3-buten-2-one, terpenyl isobutyrate, 4-(1,1-dimethylethyl)-1-cyclohexyl acetate (origin: Firmenich S A, Geneva, Switzerland), 8-methoxy-1-p-menthene, (1S,1'R)-2-[1-(3',3'-dimethyl-1'-cyclohexyl)ethoxy]-2-methylpropyl propanoate (origin: Firmenich S A, Geneva, Switzerland), para tert-butylcyclohexanone, menthenethiol, 1-methyl-4-(4-methyl-3-pentenyl)-3-cyclohexene carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), a mixture of (1 RS,2SR,6RS,7RS,8SR)-tricyclo[5.2.1.0~2,6~]dec-3-en-8-yl 2-methylpropanoate and (1 RS,2SR,6RS,7RS,8SR)-tricyclo[5.2.1.0~2,6~]dec-4-en-8-yl 2-methylpropanoate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), a mixture of 3-(3,3-dimethyl-5-indanyl)propanal and 3-(1,1-dimethyl-5-indanyl)propanal (origin: Firmenich S A, Geneva, Switzerland), 3',4-dimethyl-tricyclo[6.2.1.0(2,7)]undec-4-ene-9-spiro-2'-oxirane (origin: Firmenich S A, Geneva, Switzerland), 9/10-ethyldiene-3-oxatricyclo[6.2.1.0(2,7)]undecane, (perhydro-5,5,8A-trimethyl-2-naphthalenyl) acetate (origin: Firmenich S A, Geneva, Switzerland), octalynol, (dodecahydro-3a,6,6,9a-tetramethyl-naphtho[2,1-b]furan, origin: Firmenich S A, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, pinene, camphene, 8-methoxycedrane, (8-methoxy-2,6,6,8-tetramethyl-tricyclo[5.3.1.0(1,5)]undecane (origin: Firmenich S A, Geneva, Switzerland), cedrene, cedrenol, cedrol, mixture of 9-ethylidene-3-oxatricyclo[6.2.1.0(2,7)]undecan-4-one and 10-ethylidene-3-oxatricyclo[6.2.1.0(2,7)]undecan-4-one (origin: Firmenich S A, Geneva, Switzerland), 3-methoxy-7,7-dimethyl-10-methylene-bicyclo[4.3.1]decane (origin: Firmenich SA, Geneva, Switzerland);

Group 6: (trimethyl-13-oxabicyclo-[10.1.0]-trideca-4,8-diene (origin: Firmenich S A, Geneva, Switzerland), Ambrettolide LG ((E)-9-hexadecen-16-olide, origin: Firmenich S A, Geneva, Switzerland), pentadecenolide (origin: Firmenich S A, Geneva, Switzerland), muscenone (3-methyl-(4/5)-cyclopentadecenone, origin: Firmenich S A, Geneva, Switzerland), 3-methylcyclopentadecanone (origin: Firmenich S A, Geneva, Switzerland), pentadecanolide (origin: Firmenich S A, Geneva, Switzerland), cyclopentadecanone (origin: Firmenich S A, Geneva, Switzerland), 1-ethoxyethoxy) cyclododecane (origin: Firmenich S A, Geneva, Switzerland), 1,4-dioxacycloheptadecane-5,17-dione, 4,8-cyclododecadien-1-one;

Group 7: (+−)-2-methyl-3-[4-(2-methyl-2-propanyl)phenyl]propanal (origin: Givaudan S A, Vernier, Switzerland), 2,2,2-trichloro-1-phenylethyl acetate.

Preferably, the perfume comprises at least 30%, preferably at least 50%, more preferably at least 60% of ingredients selected from Groups 1 to 7, as defined above. More preferably said perfume comprises at least 30%, preferably at least 50% of ingredients from Groups 3 to 7, as defined above. Most preferably said perfume comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a log P above 3, preferably above 3.5 and even more preferably above 3.75.

Preferably, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols. According to an embodiment, the oil phase (or the oil-based core) comprises:
- 25-100 wt % of a perfume oil comprising at least 15 wt % of high impact perfume raw materials having a Log T<−4, and 0-75 wt % of a density balancing material having a density greater than 1.07 g/cm$^3$. The nature of high impact perfume raw materials having a Log T<−4 and density balancing material having a density greater than 1.07 g/cm3 are described in WO2018115250, the content of which are included by reference.

According to a particular embodiment, the hydrophobic material is free of any active ingredient (such as perfume). According to this particular embodiment, it comprises, preferably consists of hydrophobic solvents, preferably chosen in the group consisting of isopropyl myristate, tryglycerides (e.g. Neobee® MCT oil, vegetable oils), D-limonene, silicone oil, mineral oil, and mixtures thereof with optionally hydrophilic solvents preferably chosen in the group consisting of 1,4 butanediol, benzyl alcohol, triethyl citrate, triacetin, benzyl acetate, ethyl acetate, propylene glycol (1,2-propanediol), 1,3-Propanediol, dipropylene glycol, glycerol, glycol ethers and mixtures thereof.

The term "biocide" refers to a chemical substance capable of killing living organisms (e.g. microorganisms) or reducing or preventing their growth and/or accumulation. Biocides are commonly used in medicine, agriculture, forestry, and in industry where they prevent the fouling of, for example, water, agricultural products including seed, and oil pipelines. A biocide can be a pesticide, including a fungicide, herbicide, insecticide, algicide, molluscicide, miticide and rodenticide; and/or an antimicrobial such as a germicide, antibiotic, antibacterial, antiviral, antifungal, antiprotozoal and/or antiparasite.

As used herein, a "pest control agent" indicates a substance that serves to repel or attract pests, to decrease, inhibit or promote their growth, development or their activity. Pests refer to any living organism, whether animal, plant or fungus, which is invasive or troublesome to plants or animals, pests include insects notably arthropods, mites, spiders, fungi, weeds, bacteria and other microorganisms.

The term "flavoring ingredient" or "flavor" or the like is understood to define a variety of flavor and fragrance materials of both natural and synthetic origins, including single compounds or mixtures. Specific examples of such components may be found in the literature, e.g. in Fenaroli's Handbook of Flavor Ingredients, 1975, CRC Press; synthetic Food Adjuncts, 1947 by M. B. Jacobs, edited by van Nostrand; or Perfume and Flavor Chemicals by S. Arctander 1969, Montclair, N.J. (USA). These substances are well known to the person skilled in the art of flavoring and/or aromatizing foods and consumer products.

The flavoring ingredient may be a taste modifier. A "taste modifier" is understood as an active ingredient that operates on a consumer's taste receptors, or provides a sensory characteristic related to mouthfeel (such as body, roundness, or mouth-coating) to a product being consumed. Non-limiting examples of taste modifiers include active ingredients that enhance, modify or impart saltiness, fattiness, umami, kokumi, heat sensation or cooling sensation, sweetness, acidity, tingling, bitterness or sourness.

The flavoring ingredients can be a complex flavor emulating certain organoleptic characteristics, such as sweet and savory tonalities as for example in chicken, beef, pork or shrimp flavor.

The core material may be in the liquid or solid state at temperatures from 20° C. to 30° C.

According to an embodiment, the core material is a liquid at temperatures from 20° C. to 30° C.

According to another embodiment, the core material is a solid at temperatures from 20° C. to 30° C.

The core material may be hydrophobic, meaning it is immiscible with water at temperatures from 20° C. to 30° C. and is present in the form of a separate, hydrophobic phase.

The core may comprise at least 5 wt. %, more preferably at least 10 wt. %, even more preferably at least 20 wt. %, most preferably at least 30 wt. %, e.g. at least 40 wt. % of chemical compounds possessing a vapor pressure of higher than 0.007 Pa (the vapor pressure being specified for a reference temperature of 25° C.).

Preferably, at least 10 wt. % of the core material possess a vapor pressure above 0.1 Pa, more preferably, at least 10 wt. % have a vapor pressure of >1 Pa at 25° C., and most preferably, at least 10 wt. % have a vapor pressure of >10 Pa at 25° C.

The given value of 0.007 Pa at 25° C. for the vapor pressure is generally regarded as a limiting value identifying compounds with a volatile character. For the purpose of the present invention, the vapor pressures are determined by calculation using the method disclosed in "EPI suite" software; 2000 U.S. Environmental Protection Agency.

Preferably, the core of the coacervate core-shell microcapsule comprises the flavor is ingredient. In other words, the flavor ingredient is encapsulated in the core of the coacervate core-shell microcapsule.

The core of the coacervate core-shell microcapsule may comprise a fat matrix, preferably wherein the fat matrix comprises food grade oils.

The fat matrix may comprise (i) a hydrogenated oil or (ii) a hydrogenated fat or (iii) cocoa butter or (iv) a mixture of i-iii.

Preferably, hydrogenated oils include hydrogenated palm oil, hydrogenated soybean oil and hydrogenated cottonseed oil.

Preferably, hydrogenated fat includes cocoa fat.

More preferably, the fat matrix comprises a mixture of a fat and a hydrogenated oil. Even more preferably, the fat matrix comprises a mixture of hydrogenated palm oil with coco fat and/or cocoa butter.

According to a particular embodiment, the shell of the microcapsules further comprises an additional polymeric material, wherein said polymeric material is preferably chosen in the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof.

According to an embodiment, the shell is a composite shell made of a coacervate material and a polymeric material.

According to a particular embodiment, the additional polymeric material forms an inner layer.

According to an embodiment, the microcapsules comprises an inner shell made of a polymeric material and an outer coacervate shell comprising the plant protein extract.

The shell of the microcapsule may be cross-linked using a cross-linking agent. Typically, a cross-linking agent may be used to harden the microcapsule shell.

The cross-linking agents may include formaldehyde, tannins (such as polyphenols), acetaldehyde, glutaraldehyde, glyoxal, chrome alum or transglutaminase.

Preferably, the cross-linking agent is glutaraldehyde. Glutaraldehyde is well described in the public domain and commercially available.

Preferably, the cross-linking is conducted at a temperature within the range of 5 to 40° C., preferably 15 to 25° C., more preferably 20 to 25° C.

Preferably, the pH during the cross-linking is adjusted to a level at which cross-linking can be conducted effectively. Preferably, if cross-linking is performed enzymatically using transglutaminase, the pH may be adjusted to 3 to 7, more preferably 3.5 to 5.5.

Preferably, the cross-linking is carried out for a time period of from 1 to 15 h, preferably from 2 h to 12 h, more preferably from 7 h to 10 h, in particular at ambient temperature (i.e. at 20 to 25° C.).

Alternatively, the cross-linking is carried out for a time period of from 1 to 15 h, preferably from 1 to 4 h, in particular at ambient temperature (i.e. at 20 to 25° C.).

Alternatively, the shell may also be hardened by other methods different from cross-linking using the aforementioned cross-linking agents. Such methods comprise (i) hardening of the shell by thermal annealing, which is achieved by heating the capsules; preferably, the heating is performed at a temperature close to the denaturation temperature of the protein, and most preferably at the or above the denaturation temperature of the protein; (ii) hardening the shell by a change in pH (which may be referred to as a 'pH quench') to range wherein the shell's density is increased; (iii) hardening the shell by a change in ionic strength to range wherein the protein's wherein the shell's density is increased, which may be achieved by addition of solutes, preferably by addition of salt; (iv) hardening the shell by modifying continuous water phase by addition of water-miscible additives such that the wherein the shell's density is increased, preferably by addition of glycerol, propylene glycol, ethanol or isopropanol; (v) hardening the shell by any combination of methods i-iv, either in sequence, simultaneously, or by combining any of methods i-iv both in sequence and simultaneously.

According to a particular embodiment, the shell is cross-linked only by a thermal treatment.

Whereas the just-mentioned alternative methods for hardening the shell are usually thought of as destructive, disintegrating procedures for the protein itself, surprisingly it was found that such procedures lead to a denser, more robust shells of the capsules due to protein being brought from its native state to a denaturated or coagulated state.

Another object of the invention is a process for preparing the coacervate core-shell microcapsules as defined above, wherein the process comprises the steps of:
a) preparing a hydrocolloid solution by dissolving at least one plant protein extract in aqueous solution, preferably water;
b) optionally, preparing a hydrocolloid solution by dissolving at least one non-protein polymer in aqueous solution, preferably water;
c) optionally, mixing the hydrocolloid solutions comprising at least one plant protein extract and at least one non-protein polymer;
d) preparing, an emulsion and/or suspension by emulsifying and/or suspending a hydrophobic material in the solution;
e) forming a colloid wall comprising the plant protein extract and optionally the non-protein polymer around the hydrophobic material present in an emulsion and/or suspension; and
f) optionally, cross-linking the colloid wall.

It is understood that any of the steps c-e may be performed sequentially or simultaneously.

In another embodiment, any one or several of the process steps c, d and e described hereabove may additionally contain a dilution step in which additional solvent, preferably water, is added to any of the solutions or their mixtures.

In a particular alternative embodiment, process step e) as described hereabove additionally comprises modifying the pH value of the mixture In a preferred embodiment, the process step e) of forming a colloid wall comprises coacervation of the plant protein extract and optionally the non-protein polymer.

While it is understood that the above order of process steps is the preferred order, it may be possible to change the order of some of the steps. In a particular alternative embodiment, step c) may be performed after step d), meaning the hydrophobic material is first emulsified in the solution prepared in step a), and the solution prepared in step b) is only added after emulsification.

According to an embodiment, the weight ratio between the plant protein extract and the non-protein polymer is comprised between 1 and 100, particularly between 1 and 10, more particularly between 1 and 5.

According to a particular embodiment, the plant protein extract is obtained by an acidic extraction of a pulse seed flour (or pulse seeds or root vegetables), carried out typically at a pH between 2 and 5, preferably between 2.5 and 3.5.

Typically, the extraction is carried out by dispersing pulse seed flour (or pulse seeds or root vegetables) in water, adjusting the pH value to a range of 1.5 to 5.5, preferably 2.5-3.5 using acid, preferably using hydrochloric acid, centrifuging said dispersion and collecting the extract which is present as the protein-rich supernatant.

According to another particular embodiment, the plant protein extract is obtained by a basic extraction of a pulse seed flour (or pulse seeds or root vegetables), carried out typically at a pH between 7 and 10, preferably between 7.5 and 9.

The first solution may comprise dissolving at least one plant protein extract, in aqueous solution, preferably water, and maintaining it at a temperature from 30° C. to 50° C., preferably from 35° C. to 45° C. and even more preferably from 38 to 42° C.

In the first solution, the protein may be present in the aqueous solution in an amount of from 0.5 to 20 wt %, more preferably from 1 to 15 wt %, even more preferably from 7 to 13 wt %.

The second solution may comprise dissolving at least one non-protein polymer, preferably gum arabic, in aqueous solution, preferably water, and maintaining it at a temperature from 30° C. to 50° C., preferably from 35° C. to 45° C. and even more preferably from 38 to 42° C.

In the second solution, the non-protein polymer may be present in the aqueous solution in an amount from 0.5 to 20 wt %, more preferably from 1 to 15 wt %, even more preferably from 7 to 13 wt %.

The first and second solution may be mixed under agitation to form the third solution.

The pH of the third aqueous solution may be adjusted to a pH value below 4.7, preferably below 4.3 and most preferably below 3.5.

The pH of the third aqueous solution may be adjusted by the addition of a food grade acid solution, preferably by addition of an aqueous lactic acid solution.

The hydrophobic material may be introduced into the third solution under shear to form an emulsion or suspension.

The emulsion or suspension may be prepared in a conventional manner.

The emulsion or suspension may be prepared by adding the hydrophobic material to the third solution over a period of about 3 to 10 minutes, preferably 4 to 6 minutes.

The emulsion or suspension may be prepared with an impeller stirrer being adjusted to a speed of 300 to 400 rpm. The stirrer speed may be adjusted as desired.

In this step, also known as the "coacervation" step, two separate phases may be created, namely, the coacervate phase (enriched in polymer) and the coexisting solvent (depleted of polymer). The coacervate phase may be generally composed of the plant protein extract and, optionally, the non-protein polymer.

The coacervation may be facilitated by modifying the pH, preferably in a way that the pH moves closer to the isoelectric point of the protein, preferably by starting at a pH value below the isoelectric point and increasing the pH.

If a non-protein polymer is present, the pH for coacervation is preferably adjusted such that the positive charges on the proteins are neutralized by the negative charges on the non-protein polymer.

The pH is adjusted by the addition of a food grade acid or base solution, preferably by addition of an aqueous lactic acid solution, and sodium hydroxide solution.

Phase separation may be also induced by various other ways by changing the physicochemical environment of the solution, e.g. salting out or addition of a second high-molecular weight component so as to induce phase separation, typically at a pH between 2 and 5.

According to a particular embodiment, when the core-shell microcapsule comprises an additional polymeric material, a polyfunctional monomer is added in the oil phase (in addition to the hydrophobic material) and/or in the water phase.

By "polyfunctional monomer", it is meant a molecule that, as unit, reacts or binds chemically to form a polymer or supramolecular polymer. The polyfunctional polymer of the invention has at least two functions capable of forming a microcapsule shell.

The polyfunctional monomer can be chosen in the group consisting of at least one polyisocyanate, poly maleic anhydride, poly acid chloride, polyepoxide, acrylate monomers, polyalkoxysilane, melamine-based resin and mixtures thereof.

According to a particular embodiment, the polyfunctional monomer used in the process according to the invention is present in amounts representing from 0.1 to 15%, preferably from 0.5 to 10% and more preferably from 0.8 to 6%, and even more preferably between 1 and 3% by weight of the oil phase or of the water phase.

According to a particular embodiment, the monomer added in step a) is at least one polyisocyanate having at least two isocyanate functional groups.

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

Another object of the present invention is a coacervate core-shell microcapsules obtainable by the process as defined above.

Another object of the invention is a process for preparing a microcapsule powder comprising the steps as defined above and an additional step consisting of submitting the slurry obtained in step e) or f) to a drying, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, vegetable gums, pectins, xanthans, alginates, carragenans or cellulose derivatives to provide microcapsules in a powder form.

However, one may cite also other drying method such as the extrusion, plating, spray granulation, the fluidized bed, or even a drying at room temperature using materials (carrier, desiccant) that meet specific criteria as disclosed in WO2017/134179.

According to a particular embodiment, the carrier material contains free hydrophobic material which can be same or different from the hydrophobic material from the core of the microcapsules.

Consumer Products

By "consumer product" or "end-product" it is meant a manufactured product ready to be distributed, sold and used by a consumer.

The microcapsules of the invention can be used for the preparation of perfuming or flavouring compositions which are also an object of the invention.

Flavored Consumer Products

The powder composition of the invention can be used in a great variety of edible end products. End products are more particularly a food, pet-food or feed products. As the microcapsules of the invention are plant based microcapsules, they are particularly advantageous for vegetarian meat analogues or meat replacers, vegetarian burger, sausages, patties, chicken-imitate nuggets . . . , meat products (e.g. processed meat, poultry, beef, pork, ham, fresh sausage or raw meat preparations, spiced or marinated fresh meat or cured meat products, reformed meat) or extended meat products making use of a combination of animal and vegetable protein in varying ratios, often being coextruded or a mix between textured vegetable protein and animal protein. Meat, for the purpose of the present invention, encompasses red meat, such as beef, pork, sheep, lamb, game and poultry, such as chicken, turkey, goose and duck. Preferably, the food of the present invention is meat selected from beef, poultry and pork.

In one aspect, the flavored consumer product is selected from the group consisting of: protein powders, protein drinks, protein bars, meat analogues, seefood analogues and savory goods.

Meat analogues can include pork analogues, venison analogues, beef analogues, veal analogues, rabbit analogues, sausage analogues, deli meat analogues, ham analogues, salami analogues, pepperoni analogues, chicken analogues, turkey analogues, goose analogues, pheasant analogues, pigeon analogues, whale analogues, lamb analogues, goat analogues, donkey analogues, and squirrel analogues.

Seafood analogues can include fish analogues, scallop analogues, shrimp analogues, crabmeat analogues, shellfish analogues, clam analogues, squid analogues, conch analogues, and sea pineapple analogues.

When the flavored consumer product is a particulate or powdery food, the dry particles may easily be added thereto by dry-mixing. Typical flavored articles are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

The dry particles provided herein may be suitable for conveying flavors to beverages, fluid dairy products, condiments, baked goods, frostings, bakery fillings, candy, chewing gum and other food products.

Beverages include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra-high temperature, ohmic heating or commercial aseptic sterilization) and hot-filled packaging; and cold-filled products made through filtration or other preservation techniques.

Fluid dairy products include, without limitation, non-frozen, partially frozen and frozen fluid dairy products such as, for example, milks, ice creams, sorbets and yogurts.

Condiments include, without limitation, ketchup, mayonnaise, salad dressing, Worcestershire sauce, fruit-flavored sauce, chocolate sauce, tomato sauce, chili sauce, and mustard.

Baked goods include, without limitation, cakes, cookies, pastries, breads, donuts and the like.

Bakery fillings include, without limitation, low or neutral pH fillings, high, medium or low solids fillings, fruit or milk based (pudding type or mousse type) fillings, hot or cold make-up fillings and nonfat to full-fat fillings.

Nevertheless, the microcapsules of the invention can also be of particular interest in the following examples of products:

Baked goods (e.g. bread, dry biscuits, cakes, other baked goods),

Non-alcoholic beverages (e.g. carbonated soft drinks, bottled waters, sports/energy drinks, juice drinks, vegetable juices, vegetable juice preparations), Alcoholic beverages (e.g. beer and malt beverages, spirituous beverages), Instant beverages (e.g. instant vegetable drinks, powdered soft drinks, instant coffee and tea), Cereal products (e.g. breakfast cereals, pre-cooked ready-made rice products, rice flour products, millet and sorghum products, raw or pre-cooked noodles and pasta products), Milk products (e.g. fresh cheese, soft cheese, hard cheese, milk drinks, whey, butter, partially or wholly hydrolysed milk protein-containing products, fermented milk products, condensed milk and analogues), Dairy based products (e.g. fruit or flavored yoghurt, ice cream, fruit ices)

Confectionary products (e.g. chewing gum, hard and soft candy)

Chocolate and compound coatings

Products based on fat and oil or emulsions thereof (e.g. mayonnaise, spreads, margarines, shortenings, remoulade, dressings, spice preparations), Spiced, marinated or processed fish products (e.g. fish sausage, surimi), Eggs or egg products (dried egg, egg white, egg yolk, custard), Desserts (e.g. gelatins and puddings)

Products made of soya protein or other soya bean fractions (e.g. soya milk and products made therefrom, soya lecithin-containing preparations, fermented products such as tofu or tempeh or products manufactured therefrom, soya sauces), Vegetable preparations (e.g. ketchup, sauces, processed and reconstituted vegetables, dried vegetables, deep frozen vegetables, pre-cooked vegetables, vegetables pickled in vinegar, vegetable concentrates or pastes, cooked vegetables, potato preparations), Vegetarian meat replacer, vegetarian burger Spices or spice preparations (e.g. mustard preparations, horseradish preparations), spice mixtures and, in particular seasonings which are used, for example, in the field of snacks.

Snack articles (e.g. baked or fried potato crisps or potato dough products, bread dough products, extrudates based on maize, rice or ground nuts), Meat products (e.g. processed meat, poultry, beef, pork, ham, fresh sausage or raw meat preparations, spiced or marinated fresh meat or cured meat products, reformed meat), Ready dishes (e.g. instant noodles, rice, pasta, pizza, tortillas, wraps) and soups and broths (e.g. stock, savory cube, dried soups, instant soups, pre-cooked soups, retorted soups), sauces (instant sauces, dried sauces, ready-made sauces, gravies, sweet sauces).

Preferably, the microcapsules according to the invention shall be used in products selected from the group consisting of baked goods, instant beverages, cereal products, milk products, dairy-based products, products based on fat and oil or emulsions thereof, desserts, vegetable preparations, vegetarian meat replacer, spices and seasonings, snacks, meat products, ready dishes, soups and broths and sauces.

According to a particular embodiment, the flavored product is chosen group consisting of a meat- and/or fish-based food or analogue, a stock, a savory cube, a powder mix, a beef or pork based product, a seafood, surimi, instant noodles, rice, soups, sauces, ready-made meal, frozen or chilled pizza, pasta, potato flakes or fried, noodles, a potato/tortilla chip, a microwave popcorn, nuts, a bretzel, a rice cake, a rice cracker, fermented dairy analogue beverage, acidified dairy analogue beverage, non-fermented dairy analogue beverage, cheese or cheese analogue, yoghurt or yoghurt analogue, nutritional supplement, nutritional bar, cereal, ice cream, dairy-free ice cream, confectionary product, chewing gum, hard-boiled candy and powdered drinks.

According to one embodiment, the food, pet-food or feed product comprises between 0.01 and 10% by weight, preferably between 0.1 and 5% by weight of the microcapsules of the invention.

Typically the food, pet-food or feed product further comprises proteins notably vegetable proteins or animal proteins, and mixtures thereof.

Advantageously the vegetable proteins are preferably selected among soy protein, corn, peas, canola, sunflowers, sorghum, rice, amaranth, potato, tapioca, arrowroot, chickpeas, lupins, canola, wheat, oats, rye, barley, and mixtures thereof.

The microcapsules of the invention are particularly suitable for extruded and/or baked food, pet-food or feed products more particularly comprising animal and/or vegetable proteins. Typically, said extruded and/or baked food, pet-food or feed products may be selected among meat- and/or fish-based food or analogue and mixtures thereof (in other words, meat-based food and/or fish-based food or meat analogue or fish analogue and mixtures thereof); extruded and/or baked meat analogue or extruded and/or baked fish analogue are preferred. Non-limiting examples of extruded and/or baked food, pet-food or feed products are snack products or extruded vegetable proteins with the aim to texture the protein from which meat analogous (e.g. burgers) are prepared from. The powder composition can be added pre-extrusion or after extrusion to either, the non-extruded vegetable protein isolate/concentrate or to the textured vegetable protein from which a burger or nugget (etc.) is formed.

Perfumed Consumer Products

The microcapsules of the invention can be used in combination with active ingredients. An object of the invention is therefore a composition comprising:
(i) microcapsules as defined above;
(ii) an active ingredient, preferably chosen in the group consisting of a cosmetic ingredient, skin caring ingredient, perfume ingredient, flavor ingredient, malodour counteracting ingredient, bactericide ingredient, fungicide ingredient, pharmaceutical or agrochemical ingredient, a sanitizing ingredient, an insect repellent or attractant, and mixtures thereof.

The microcapsules of the invention can also be added in different perfumed consumer products.

In particular a perfuming composition comprising (i) microcapsules as defined above; (ii) at least one perfuming co-ingredient; and (iii) optionally a perfumery adjuvant, is another object of the invention.

By "perfuming co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor. The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds (such as properfume). Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-(dodecylthio)octan-4-one, 2-phenylethyl oxo(phenyl)acetate, 3,7-dimethylocta-2,6-dien-1-yl oxo(phenyl)acetate, (Z)-hex-3-en-1-yl oxo(phenyl)acetate, 3,7-dimethyl-2,6-octadien-1-yl hexadecanoate, bis(3,7-dimethylocta-2,6-dien-1-yl) succinate, (2-((2-methylundec-1-en-1-yl)oxy)ethyl) benzene, 1-methoxy-4-(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-1-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl) naphthalene, (2-phenethoxyvinyl)benzene, 2-(1-((3,7-dimethyloct-6-en-1-yl)oxy)prop-1-en-2-yl)naphthalene, (2-((2-pentylcyclopentylidene)methoxy)ethyl)benzene or a mixture thereof.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsules as defined above.

The invention's microcapsules can advantageously be used in many application fields and used in consumer products. Microcapsules can be used in liquid form applicable to liquid consumer products as well as in powder form, applicable to powder consumer products.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:
from 2 to 65% by weight, relative to the total weight of the consumer product, of at least one surfactant;
water or a water-miscible hydrophilic organic solvent; and
a perfuming composition or microcapsules as defined above, wherein the hydrophobic material comprises a perfume is another object of the invention.

Also a powder consumer product comprising
from 2 to 65% by weight, relative to the total weight of the consumer product, of at least one surfactant; and
a perfuming composition or microcapsules, wherein the hydrophobic material comprises a perfume as defined above is part of the invention.

According to a particular embodiment, the process for preparing the microcapsules comprised in the perfumed consumer product comprises a cross-linking step as defined above (chemically and/or enzymatically) to improve the stability in challenging bases comprising a high amount of surfactants.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumed consumer product can be a perfume, such as a fine perfume, a cologne, an after-shave lotion, a body-splash; a fabric care product, such as a liquid or solid detergent, tablets and pods, a fabric softener, a dryer sheet, a fabric refresher, an ironing water, or a bleach; a personal-care product, such as a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.); a hygiene product such as sanitary napkins, diapers, toilet paper.

Another object of the invention is a consumer product comprising:
a personal care active base, and
microcapsules as defined above or the perfuming composition as defined above,
wherein the consumer product is in the form of a personal care composition.

Personal care active base in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

The personal care composition is preferably chosen in the group consisting of a hair-care product (e.g. a shampoo, hair conditioner, a colouring preparation or a hair spray), a cosmetic preparation (e.g. a vanishing cream, body lotion or a deodorant or antiperspirant), a skin-care product (e.g. a perfumed soap, shower or bath mousse, body wash, oil or gel, bath salts, or a hygiene product), oral care product (toothpaste or mouthwash composition) or a fine fragrance product (e.g. Eau de Toilette—EdT).

Another object of the invention is a consumer product comprising:
a home care or a fabric care active base, and
microcapsules as defined above or the perfuming composition as defined above, wherein the consumer product is in the form of a home care or a fabric care composition.

Home care or fabric care bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

The home or fabric care composition is preferably chosen in the group consisting fabric softener, liquid detergent, powder detergent, liquid scent booster solid scent booster.

For liquid consumer product mentioned below, by "active base", it should be understood that the active base includes active materials (typically including surfactants) and water.

For solid consumer product mention below, by "active base", it should be understood that the active base includes active materials (typically including surfactants) and optionally auxiliary agents (such as bleaching agents, buffering agent; builders; soil release or soil suspension polymers; granulated enzyme particles, corrosion inhibitors, antifoaming, sud suppressing agents; dyes, fillers, and mixtures thereof).

Fabric Softener

An object of the invention is a consumer product in the form of a fabric softener composition comprising:
- a fabric softener active base; preferably comprising at least one active material chosen in the group consisting of dialkyl quaternary ammonium salts, dialkyl ester quaternary ammonium salts (esterquats), Hamburg esterquat (HEQ), TEAQ (triethanolamine quat), silicones and mixtures thereof, the active base being used preferably in an amount comprised between 85 and 99.95% by weight based on the total weight of the composition,
- a microcapsule slurry as defined above, preferably in an amount comprised between 0.05 to 15 wt %, more preferably between 0.1 and 5 wt % by weight based on the total weight of the composition,
- optionally free perfume oil.

Liquid Detergent

An object of the invention is a consumer product in the form of a liquid detergent composition comprising:
- a liquid detergent active base; preferably comprising at least one active material chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, the active base being used preferably in an amount comprised between 85 and 99.95% by weight based on the total weight of the composition,
- a microcapsule slurry as defined above, preferably in an amount comprised between 0.05 to 15 wt %, more preferably between 0.1 and 5 wt % by weight based on the total weight of the composition,
- optionally free perfume oil.

Solid Detergent

An object of the invention is a consumer product in the form of a solid detergent composition comprising:
- a solid detergent active base; preferably comprising at least one active material chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, the active base being used preferably in an amount comprised between 85 and 99.95% by weight based on the total weight of the composition,
- a microcapsule powder or microcapsule slurry as defined above, preferably in an amount comprised between 0.05 to 15 wt %, more preferably between 0.1 and 5 wt % by weight based on the total weight of the composition,
- optionally free perfume oil.

Shampoo/shower gel

An object of the invention is a consumer product in the form of a shampoo or a shower gel composition comprising:
- a shampoo or a shower gel active base; preferably comprising at least one active material chosen in the group consisting of sodium alkylether sulfate, ammonium alkylether sulfates, alkylamphoacetate, cocamidopropyl betaine, cocamide MEA, alkylglucosides and aminoacid based surfactants and mixtures thereof, the active base being used preferably in an amount comprised between 85 and 99.95% by weight based on the total weight of the composition,
- a microcapsule slurry as defined above, preferably in an amount comprised between 0.05 to 15 wt %, more preferably between 0.1 and 5 wt % by weight based on the total weight of the composition,
- optionally free perfume oil.

Rinse-Off Conditioner

An object of the invention is a consumer product in the form of a rinse-off conditioner composition comprising:
- a rinse-off conditioner active base; preferably comprising at least one active material chosen in the group consisting of cetyltrimonium chloride, stearyl trimonium chloride, benzalkonium chloride, behentrimonium chloride and mixture thereof, the active base being used preferably in an amount comprised between 85 and 99.95% by weight based on the total weight of the composition,
- a microcapsule slurry as defined above, preferably in an amount comprised between 0.05 to 15 wt %, more preferably between 0.1 and 5 wt % by weight based on the total weight of the composition,
- optionally free perfume oil.

Solid Scent Booster

An object of the invention is a consumer product in the form of a solid scent booster composition comprising:
- a solid carrier, preferably chosen in the group consisting of urea, sodium chloride, sodium sulphate, sodium acetate, zeolite, sodium carbonate, sodium bicarbonate, clay, talc, calcium carbonate, magnesium sulfate, gypsum, calcium sulfate, magnesium oxide, zinc oxide, titanium dioxide, calcium chloride, potassium chloride, magnesium chloride, zinc chloride, saccharides such as sucrose, mono-, di-, and polysaccharides and derivatives such as starch, cellulose, methyl cellulose, ethyl cellulose, propyl cellulose, polyols/sugar alcohols such as sorbitol, maltitol, xylitol, erythritol, and isomalt, PEG, PVP, citric acid or any water soluble solid acid, fatty alcohols or fatty acids and mixtures thereof,
- a microcapsule slurry as defined above, in a powdered form, preferably in an amount comprised between 0.05 to 15 wt %, more preferably between 0.1 and 5 wt % by weight based on the total weight of the composition,
- optionally free perfume oil.

Liquid Scent Booster

An object of the invention is a consumer product in the form of a liquid scent booster composition comprising:
- an aqueous phase,
- a surfactant system essentially consisting of one or more than one non-ionic surfactant, wherein the surfactant system has a mean HLB between 10 and 14, preferably chosen in the group consisting of ethoxylated aliphatic alcohols, POE/PPG (polyoxyethylene and polyoxypropylene) ethers, mono and polyglyceryl esters, sucrose ester compounds, polyoxyethylene hydroxylesters, alkyl polyglucosides, amine oxides and combinations thereof;
a linker chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof, and
a microcapsule slurry as defined above, in the form of a slurry, preferably in an amount comprised between 0.05 to 15 wt %, more preferably between 0.1 and 5 wt % by weight based on the total weight of the composition, optionally free perfume oil.

Hair Coloration

An object of the invention is a consumer product in the form of an oxidative hair coloring composition comprising:
an oxidizing phase comprising an oxidizing agent and an alkaline phase comprising an alkakine agent, a dye precursor and a coupling compound; wherein said dye precursor and said coupling compound form an oxidative hair dye in the presence of the oxidizing agent, preferably in an amount comprised between 85 and 99.95% by weight based on the total weight of the composition,
microcapsules as defined above, preferably in an amount comprised between 0.05 to 15 wt %, more preferably between 0.1 and 5 wt % by weight based on the total weight of the composition,
optionally free perfume oil Perfuming Composition According to a particular embodiment, the consumer product is in the form of a perfuming composition comprising:
0.1 to 30%, preferably 0.1 to 20% of microcapsules as defined previously,
0 to 40%, preferably 3-40% of perfume, and
20-90%, preferably 40-90% of ethanol, by weight based on the total weight of the perfuming composition.

The invention will now be further described by way of examples. It will be appreciated that the invention as claimed is not intended to be limited in any way by these examples.

Example 1

Preparation of Core/Shell Microcapsules According to the Invention

A mixture of 10% w/w defatted soy flour and 15 Mm sodium metabisulfite was prepared in 100 mL demineralized water. The pH value was adjusted to 2.7 with 1M HCl and the mixture was stirred for 1 hour.

The pH value slightly increased to 2.9 and was re-adjusted again to 2.8.

The resulting mixture was centrifuged at 10'000 g during 30 minutes, and the supernatant (named 'solution 1' for the remainder of this example) was used for the further processing steps.

A 1 ml aliquot of the supernatant was used to determine the remaining mass fraction of protein using thermogravimetric analysis.

Separately, a solution of Gum Arabic (Efficacia®, from Nexira, 'Solution 2') is prepared at a concentration of either 10% w/w or 15% w/w.

100 g of solution 1 and 100 g of solution 2 are added to 340 g of warm demineralized water under mechanical shear, and the pH is readjusted to 2.7 using 1M HCl, and the mixture is maintained at 30° C. during 15 min.

An amount of 60 g of the flavor composition (limonene oil) to be encapsulated was slowly added to the mixture and homogenised at 230 RPM during 5 min, so as to reach an average droplet size of 150 μm, as verified by light microscopy. The stirring speed was slightly decreased, and 0.102 g of glutaraldehyde (aq.50% wt. Supplied by Sigma-Aldrich) was added to the mixture. The microcapsule suspension is mixed during 4 to 10 hours at 20-25° C.

Figure 1:
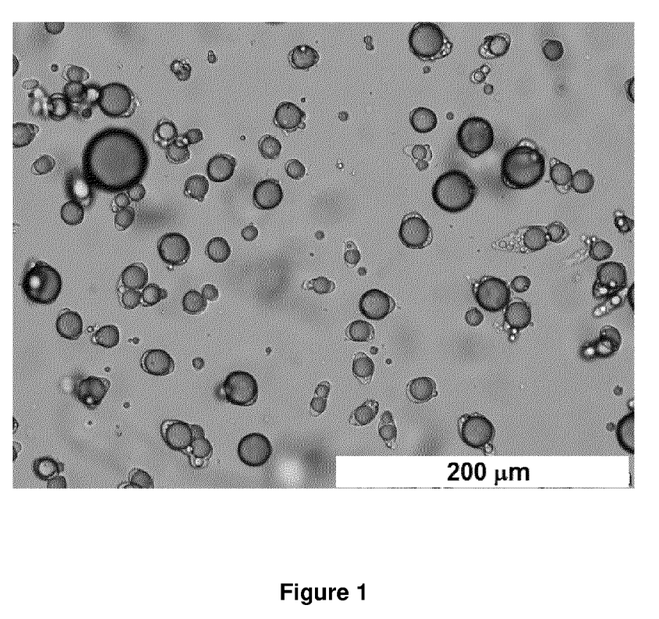
FIG. 1: Coacervate core-shell microcapsules according to the invention.
Figure 2:
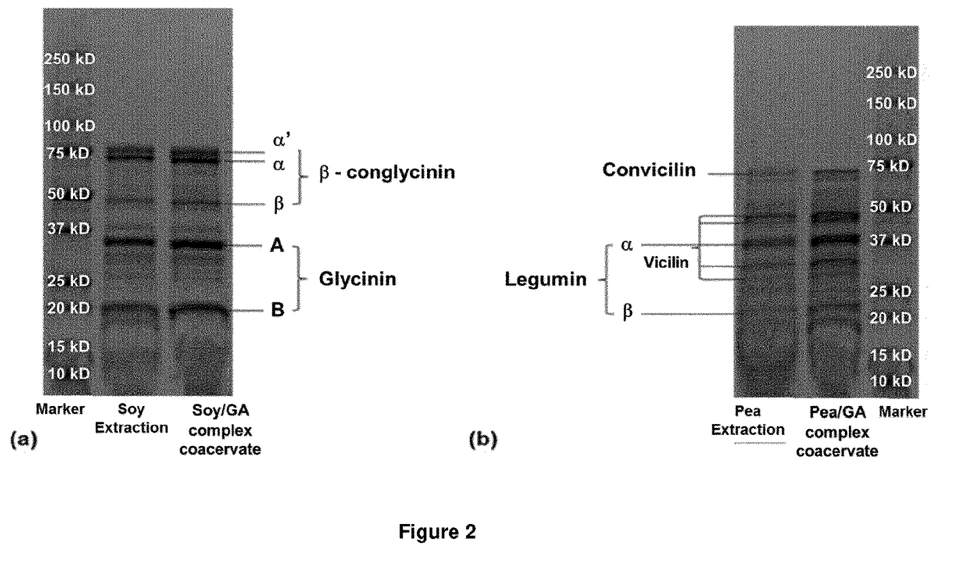
FIG. 2: SDS-PAGE (a) of the extract obtained from soy flour and of the resulting complex coacervate with Gum Arabic, and (b) of the extract obtained from pea flour and of the complex coacervate obtained from this extract with Gum Arabic FIG. 3. Rheological experiments and image of soy polymer/Gum Arabic complex coacervates undergoing hardening by heating. Temperature ramp on soy polymer/Gum Arabic complex coacervates, shown are the elastic modulus (G') and viscous modulus (G") upon heating up and subsequent cooling. Filled symbols: G', empty symbols: G".

The result was an aqueous suspension or slurry of microcapsules (see FIG. 1).

Example 2

Comparative Example Using a Soy Protein Isolate

As a comparative example, an encapsulation experiment as described in Example 1 was performed, but instead of using the protein extract as described in the present invention, a standard commercial soy protein isolate (SPI) was used. A solution of SPI (Dupont, 'Solution 1') was prepared at a concentration of 10% w/w in demineralized water. Separately, a solution of Gum Arabic (Efficacia®, from Nexira, 'Solution 2') is prepared at a concentration of either 10% w/w or 15% w/w.

100 g of solution 1 and 100 g of solution 2 are added to 340 g of warm demineralized water under mechanical shear, and the pH was readjusted to 2.7 using 1M HCl. The mixture was maintained at 30° C. during 15 min.

An amount of 60 g of the flavor composition (limonene oil) to be encapsulated was slowly added to the mixture and homogenised at 230 RPM during 5 min, so as to reach an average droplet size of 150 μm, as verified by light microscopy. The stirring speed was slightly decreased, and 0.102 g of glutaraldehyde (aq.50% wt. Supplied by Sigma-Aldrich) is added to the mixture. The microcapsule suspension was mixed during 4 to 10 hours at 20-25° C.

Unlike for Example 1, no microcapsules were obtained in this case and instead an emulsion of non-encapsulated oil drops alongside free particles is obtained.

Example 3

Preparation of Core/Shell Microcapsules According to the Invention Using Pea Flour and Gum Arabic A mixture of 10% w/w pea flour (AM Nutrition, 14% protein) and 0.285 g sodium metabisulfite (15 mM) was prepared in 100 mL demineralized water. The pH value was adjusted to 2.7 with 1M HCl and the mixture was stirred for 1 hour. The pH value slightly increased to around 2.9 and was re-adjusted again to 2.8. The resulting mixture was centrifuged at 10'000 g for 30 minutes, collect the supernatant, which contains soluble pea protein and carbohydrate. The supernatant was then freeze dried for storage. 100 mL supernatant contains 1.675 g dried polymer which includes protein and carbohydrate.

A solution was prepared by mixing a pea polymer solution and Gum Arabic (Sigma-Aldrich) solutions. 10 mL pea polymer solution (pH 3, 0.02 g/mL) was mixed with 10 mL gum arabic solution (pH 3) (pea polymer:Gum Arabic=1:0.3). Mixture is added to warm demineralized water under mechanical shear, and the pH was readjusted to 2.7 using 1M HCl and maintained at 30° C. during 15 min.

Flavor composition (limonene oil) to be encapsulated was slowly added to the mixture and homogenised at 230 RPM during 5 min. The stirring speed was slightly decreased, and glutaraldehyde (aq.50% wt. Supplied by Sigma-Aldrich) was added to the mixture. The microcapsule suspension is mixed during 4 to 10 hours at 20-25° C.

Example 4

Preparation of Core/Shell Microcapsules According to the Invention Using Pea or Soy Protein Extract and Chitosan Alkali extraction of proteins from soy and pea flour was performed like in the examples 1 and 3, but at pH 8, followed by a change of pH to pH 5.8 and mixing with the oppositely charged chitosan. Chitosan was pre-solubilized at pH around 2 to 3 and adjusted back to pH 5.8 before use. Flavor composition (limonene oil) to be encapsulated was slowly added to the mixture and homogenised at 230 RPM during 5 min. The stirring speed was slightly decreased, and glutaraldehyde (aq.50% wt. Supplied by Sigma-Aldrich) was added to the mixture. The microcapsule suspension is mixed during 4 to 10 hours at 20-25° C.

A colloidal wall material was formed via complex coacervation by using the same protein and polysaccharide concentrations as in the examples 1 and 3.

Example 5

SDS-PAGE Characterization of the Plant Protein Extracts the Complex Coacervates Obtained Therefrom with Gum Arabic The protein extracts obtained from soy flour and from pea flour, as well as the resulting complex coacervates with Gum Arabic, with the coacervates prepared according to Examples 1 and 3, were further analyzed by SDS-PAGE to obtain more information about the protein composition of the both the extracts and the coacervates. The methods and reference data on proteins from soy and pea can be found in the publications by Lam, A. C. Y., et al. "Pea protein isolates: Structure, extraction, and functionality, Food reviews international 34.2 (2018), pages 126-147, and Bogracheva, T. Ya, N. Yu Bespalova, and A. L. Leont'ev. "Isolation of 11S and 7S globulins from seeds of *glycine max*." Applied Biochemistry and Microbiology 32.4 (1996), pages 429-433. Globulins (glycinin and beta-conglycinin) take up 80% of soy protein. The fractions expected according to the two cited references have been found in both the extract and coacervate, including the smaller subunits of the proteins. These data confirm not only the quality of the protein extracts obtained here, but they clearly reveal that indeed the complex coacervates obtained according to the invention contain the exact protein fractions of the corresponding proteins, providing a confirmation of the composition of these complex coacervates.

Example 6

Crosslinking of Coacervate Capsules

Capsules were prepared according the Example 1, and the resulting capsule were then crosslinked. The capsule slurry resulting from Example 1 was processed further at 20° C. by adding a crosslinker, glutaraldehyde solution (aq.50% wt. Supplied by Sigma-Aldrich) is added to the mixture at a concentration of 0.068% w/w. Cross-linking is allowed to proceed for 4 to 10 hours at 20° C.

Example 7

Hardening of a Coacervate According to the Invention by Increasing the Temperature Capsules according the Example 1 were prepared and hardened with an additional a heating step, thereby densifying the coacervate shells. 300 ml of a capsule slurry prepared according to Example 1 was heated from 20° C. to 80° C. during 1 hour, and kept at 80° C. during 5 minutes, and let to cool down to 20° C.

To mimic the conditions during this heating step and to measure the rheological properties of the complex coacervate, the coacervate shell material was also measured using oscillatory shear rheology (a method well suited and documented to characterize such properties, as summarized for example in the books "*The Structure and Rheology Complex Fluids*", R. G. Larson, Oxford University Press, 1998, and "Understanding Rheology", F. A. Morrison, Oxford University Press 2001). The properties measured are the elastic modulus (also called 'storage modulus' in some publications), which represents the elastic behaviour of the material for a given frequency and amplitude of deformation and which is conventionally written as G', and the viscous modulus (also called 'loss modulus' in some publications), which represents the viscous behaviour of the material for a given frequency and amplitude of deformation, and which is conventionally written as G"; the units of G' and G" are Pascal (Pa).

Figure 3:
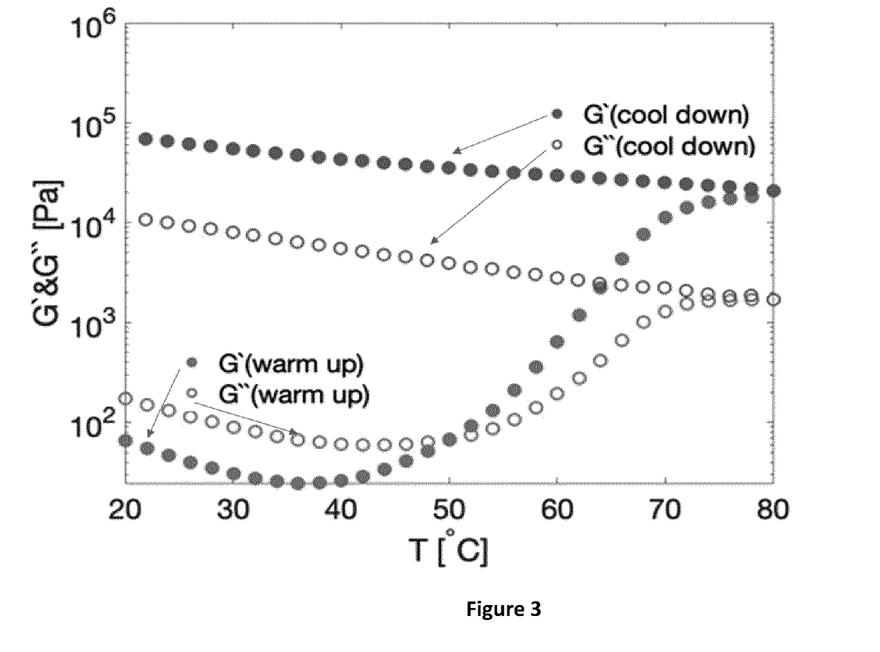

A heating ramp was performed in the rheometer (Anton Paar MCR 501 equipped with a 25 mm cone-plate geometry, Peltier temperature control, solvent trap to prevent water evaporation, as described in the books cited in the previous paragraph). The coacervate shell material resulting from the complex coacervation of soy protein extract and Gum Arabic was placed in the rheometer geometry and the temperature was increased from 20° C. to 80° C. during 1 hour, kept at 80° C. during 5 minutes, and finally decreased again with the same rate, just as described above for the heating step of the capsules. The results are shown in FIG. 3, clearly showing that complex coacervate shell material undergoes a transition from a liquid-like material (G">G', meaning the viscous modulus is initially higher than the elastic modulus) to a solid-like material (G'>G", meaning during the heating the elastic modulus becomes higher than the viscous modulus) at a temperature of 50° C., and reaching a plateau with near-constant G' and G" around 70° C. Upon cooling, the material remains solid-like at all times and the elastic modulus G' remains higher than the viscous modulus G", with the modulus still increasing further during the cooling down and reaching a value for the elastic modulus around $10^5$ Pa. These data proof that hardening by a temperature increase indeed transforms the original liquid-like coacervate into a solid-like shell.

Example 8

Preparation of Food Products Containing Capsules Prepared According to the Invention, and Comparison with Comparative Capsules Model flavor was encapsulated according to the invention as described in Example 1, and for comparison the same was done with soy protein isolate (instead of the soy protein extract obtained by acidic extract), as described in Example 2. 1 g of each of the resulting flavor slurries were added to a commercial fermented dairy analogue product (soy milk based yoghurt) by stirring and left to rest for 24 hours in the refrigerator. Organoleptic evaluation revealed that the flavor was already strongly perceived olfactively for the product flavored with the comparative flavor slurry from Example 2, even before actually tasting the product. In contrast, the encapsulated flavor from Example 1, prepared according to the invention, was only perceived upon tasting the product, thereby confirming that these flavor capsules provide protection and localization of the flavor in the complex product matrix such as a dairy analogue food product.

Similarly, the capsules prepared according to the invention from Example 1 were also compared to a comparative flavor slurry from Example 2 in a mayonnaise-type sauce (Thomy Mayonnaise Extra Light, obtained from a local supermarket), containing 1 g of flavor slurry as per examples 1 or 2 per 100 g of product, with the flavored sauce samples stored in for 24 h after preparation. Like for the dairy analogue evaluation, the encapsulated flavor according to the invention as in Example 1 was only released significantly upon degustation of the product, thereby confirming successful encapsulation and release whereas the flavor from Example 2 was already present throughout the product and revealed a strong smell even before degustation.

The invention claimed is:

1. A coacervate core-shell microcapsule comprising a hydrophobic material, wherein:
    a) the hydrophobic material is encapsulated in the core of the coacervate core-shell microcapsule, and
    b) the shell of the coacervate core-shell microcapsule comprises at least one plant protein extract and optionally a non-protein polymer;
wherein the content of protein in the plant protein extract is less than 55% by weight.

2. The microcapsule according to claim 1, wherein the plant protein extract is chosen in the group consisting of protein extracts from soy, pea, wheat, rice, potato, quinoa, amaranth, lentil, hemp, oat, buckwheat, chick pea, lupin seeds, canola, flaxseed and mixtures thereof.

3. The microcapsule according to claim 1, wherein the non-protein polymer is chosen in the group consisting of gum arabic, carboxymethylcellulose, chitosan, xanthan, agar, alginate salts, pectinate salts or carrageenan.

4. The microcapsule according to claim 1, wherein the plant protein extract is a soy protein extract and wherein the non-protein polymer is Gum Arabic.

5. The microcapsule according to claim 1, wherein the shell of the microcapsule is cross-linked using formaldehyde, tannins, acetaldehyde, glutaraldehyde, glyoxal, chrome alum, transglutaminase and mixtures thereof.

6. The microcapsule according to claim 1, wherein the ratio between the plant protein extract and the non-protein polymer is comprised between 1 and 100.

7. The microcapsule according to claim 1, wherein the shell comprises an additional polymeric material.

8. The microcapsule according to claim 7, wherein the polymeric material is chosen in the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof.

9. A process for preparing the coacervate core-shell microcapsule as defined in claim 1, wherein the process comprises the steps of:
    a) preparing a hydrocolloid solution by dissolving at least one plant protein extract in aqueous solution;
    b) optionally, preparing a hydrocolloid solution by dissolving at least one non-protein polymer in aqueous solution;
    c) optionally, mixing the hydrocolloid solutions comprising at least one plant protein extract and at least one non-protein polymer;
    d) preparing an emulsion and/or suspension by emulsifying and/or suspending a hydrophobic material in the solution;
    e) forming a colloid wall comprising the plant protein extract and optionally the non-protein polymer around droplets and/or particles of the hydrophobic material present in an emulsion and/or suspension; and
    f) optionally, cross-linking the colloid wall.

10. The process according to claim 9, wherein the plant protein extract is obtained by an acidic extraction or an alkali extraction of a pulse seed flour, pulse seeds, or root vegetables.

11. The process according to claim 10, wherein the extraction is an acidic extraction.

12. A consumer product comprising the coacervate core-shell microcapsule according to claim 1, wherein said product is a flavoured or fragranced product.

13. The consumer product according to claim 12, wherein the fragranced product is chosen in the group consisting of a liquid or solid detergent, a fabric softener, liquid or solid scent-boosters, a shampoo, a shower gel, a hair conditioning product, a deodorant or antiperspirant.

14. The consumer product according to claim 12, wherein the flavored product is chosen in the group consisting of a meat- and/or fish-based food or analogue, a stock, a savory cube, a powder mix, a beef or pork based product, a seafood, surimi, instant noodles, rice, soups, sauces, ready-made meal, frozen or chilled pizza, pasta, potato flakes or fried, noodles, a potato/tortilla chip, a microwave popcorn, nuts, a bretzel, a rice cake, a rice cracker, fermented dairy analogue beverage, acidified dairy analogue beverage, non-fermented dairy analogue beverage, cheese or cheese analogue, yoghurt or yoghurt analogue, nutritional supplement, nutritional bar, cereal, ice cream, dairy-free ice cream, confectionary product, chewing gum, hard-boiled candy and powdered drinks.

15. The microcapsule according to claim 1, wherein the hydrophobic material is a flavor or a perfume.

16. The microcapsule according to claim 1, wherein
    the plant protein extract is chosen in the group consisting of protein extracts from soy, pea, wheat, rice, potato, quinoa, amaranth, lentil, hemp, oat, buckwheat, chick pea, lupin seeds, canola, flaxseed and mixtures thereof; and
    the non-protein polymer is chosen in the group consisting of gum arabic, carboxymethylcellulose, chitosan, xanthan, agar, alginate salts, pectinate salts or carrageenan.

17. The process according to claim 9, wherein the aqueous solutions are water.

18. The process according to claim 11, wherein the extraction is carried out at a pH comprised between 2 and 5.

* * * * *